(12) United States Patent
Chi et al.

(10) Patent No.: US 10,153,442 B2
(45) Date of Patent: Dec. 11, 2018

(54) IRIDIUM COMPLEX, OLED USING THE SAME, AND NITROGEN-CONTAINING TRIDENTATE LIGAND HAVING CARBENE UNIT

(71) Applicant: National Tsing Hua University, Hsinchu (TW)

(72) Inventors: Yun Chi, Hsinchu (TW); Jun Lin, Taoyuan (TW)

(73) Assignee: National Tsing Hua University, Hsinchu (TW)

( * ) Notice: Subject to any disclaimer, the term of this patent is extended or adjusted under 35 U.S.C. 154(b) by 356 days.

(21) Appl. No.: 15/099,290

(22) Filed: Apr. 14, 2016

(65) Prior Publication Data
US 2017/0194575 A1    Jul. 6, 2017

(30) Foreign Application Priority Data

Dec. 31, 2015    (TW) .............................. 104144592 A (51) Int. Cl.
*H01L 51/00*    (2006.01)
*C07F 15/00*    (2006.01)
(Continued)

(52) U.S. Cl.
CPC ........ *H01L 51/0085* (2013.01); *C07D 401/04* (2013.01); *C07F 15/0033* (2013.01);
(Continued)

(58) Field of Classification Search
CPC .......................... H01L 51/0085; C07D 401/04
See application file for complete search history.

(56) References Cited

U.S. PATENT DOCUMENTS

2005/0260449 A1    11/2005    Walters et al.
2007/0141397 A1*    6/2007    Watanabe ............ C07D 213/81
                                                          428/690
(Continued)

FOREIGN PATENT DOCUMENTS

CN    102268250    12/2011
TW    200740832    11/2007
(Continued)

OTHER PUBLICATIONS

"Office Action of Taiwan Counterpart Application," dated Mar. 24, 2017, p. 1-p. 7.

*Primary Examiner* — Michael M Dollinger
(74) *Attorney, Agent, or Firm* — J.C. Patents (57) ABSTRACT

An iridium complex and an OLED using the same are shown. The iridium complex is represented by formula (I),

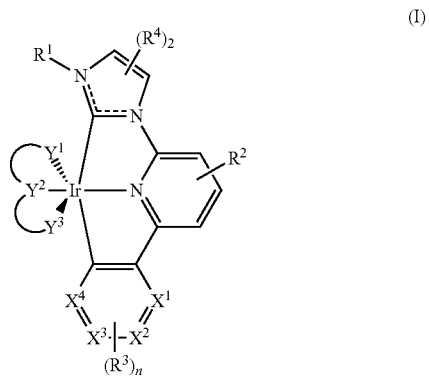

wherein $R^1$ is substituted or unsubstituted $C_{1-12}$ alkyl, or substituted or unsubstituted $C_{6-12}$ aryl; $R^2$ is hydrogen,
(Continued)

fluorine or —$C_mF_{2m+1}$ (m=1, 2 or 3), substituted or unsubstituted $C_{1-12}$ alkyl, or substituted or unsubstituted $C_{6-12}$ aryl; $R^3$ is hydrogen, fluorine or —$C_mF_{2m+1}$ (m=1, 2 or 3), substituted or unsubstituted $C_{1-6}$ alkyl or alkoxy, and n is 1, 2, 3 or 4; each of $R^4$ is hydrogen or substituted or unsubstituted $C_{1-12}$ alkyl, or $R^4$'s may join to form a $C_{3-8}$ aromatic ring, and $R_4$'s may be the same or different; $X^1$, $X^2$, $X^3$ and $X^4$ are each independently CH or nitrogen; $Y^1$, $Y^2$ and $Y^3$ are each independently carbon or nitrogen, with a proviso that at least one of $Y^1$, $Y^2$ and $Y^3$ is nitrogen, and the tridentate chelate $Y^{1\wedge}Y^{2\wedge}Y^3$ is dianionic.

11 Claims, 1 Drawing Sheet

(51) Int. Cl.
    *C07D 401/04*     (2006.01)
    *C09K 11/06*     (2006.01)
    *H01L 51/50*     (2006.01)

(52) U.S. Cl.
    CPC ........ *C09K 11/06* (2013.01); *C09K 2211/185* (2013.01); *H01L 51/5016* (2013.01)

(56) References Cited

U.S. PATENT DOCUMENTS

| | | |
|---|---|---|
| 2009/0102363 A1 | 4/2009 | Haga et al. |
| 2014/0021447 A1* | 1/2014 | Beers ................... C07D 213/74 257/40 |
| 2014/0264292 A1* | 9/2014 | Xia ....................... C07D 401/04 257/40 |
| 2015/0084028 A1 | 3/2015 | Nii et al. |

FOREIGN PATENT DOCUMENTS

| | | | |
|---|---|---|---|
| TW | I482837 | 5/2015 | |
| WO | 2012114316 | 8/2012 | |
| WO | WO-2013137221 A1 * | 9/2013 | ............. C09B 57/10 |
| WO | WO-2014077357 A1 * | 5/2014 | ........... C07F 15/0046 |

* cited by examiner

IRIDIUM COMPLEX, OLED USING THE SAME, AND NITROGEN-CONTAINING TRIDENTATE LIGAND HAVING CARBENE UNIT

CROSS-REFERENCE TO RELATED APPLICATION

This application claims the priority benefit of Taiwan application serial no. 104144592, filed on Dec. 31, 2015. The entirety of the above-mentioned patent application is hereby incorporated by reference herein and made a part of this specification.

BACKGROUND OF THE INVENTION

Field of Invention

The invention relates to an iridium complex for an organic light-emitting diode (OLED), and more particularly, to an iridium complex having a carbene fragment, an OLED using the iridium complex, and a nitrogen-containing tridentate chelate having a carbene unit that is for forming the iridium complex.

Description of Related Art

OLED devices have got much attention in the display industry, especially in the flat display industry, as allowing low-voltage driving and having high luminous efficiency.

In order to develop full-color flat displays, finding stable light emitting materials with different colors and having high luminous efficiency is important in the research of OLED. So far certain tris-bidentate iridium complexes have been report to have suitable luminescence characteristics, but the rigidity and the stability thereof are often insufficient.

SUMMARY OF THE INVENTION

In view of the foregoing, the invention provides an iridium complex having a carbene fragment, which is capable of effectively increasing the luminous efficiency when used in the light-emitting layer of an OLED.

The invention also provides an OLED adopting the iridium complex.

The invention further provides a nitrogen-containing tridentate chelate having a carbene unit that is for forming the iridium complex.

The iridium complex of the invention is represented by formula (I), (I)

wherein $R^1$ is substituted or unsubstituted $C_{1-12}$ alkyl, or substituted or unsubstituted $C_{6-12}$ aryl; $R^2$ is hydrogen, fluorine or $-C_mF_{2m+1}$ (m=1, 2 or 3), substituted or unsubstituted $C_{1-12}$ alkyl, or substituted or unsubstituted $C_{6-12}$ aryl; $R^3$ is hydrogen, fluorine or $-C_mF_{2m+1}$ (m=1, 2 or 3), substituted or unsubstituted $C_{1-6}$ alkyl, or substituted or unsubstituted $C_{1-6}$ alkoxy, and n is 1, 2, 3 or 4; each of $R^4$ is hydrogen or substituted or unsubstituted $C_{1-12}$ alkyl, or $R^4$'s may join to form a $C_{3-8}$ N-heteroaromatic or aromatic ring, and $R^4$'s may be the same or different; $X^1$, $X^2$, $X^3$ and $X^4$ are each independently CH or nitrogen; $Y^1$, $Y^2$ and $Y^3$ are each independently carbon or nitrogen, with a proviso that at least one of $Y^1$, $Y^2$ and $Y^3$ is nitrogen, and the tridentate chelate $Y^1{^\wedge}Y^2{^\wedge}Y^3$ is dianionic.

In an embodiment, $Y^1$ and $Y^2$ are nitrogen and $Y^3$ is carbon, the iridium complex being represented by formula (I-1)

(I-1)

wherein $R^1$, $R^2$, $R^3$, $R^4$, n, $X^1$, $X^2$, $X^3$ and $X^4$ are defined as above. It is possible that $X^1$, $X^2$, $X^3$ and $X^4$ are all CH or that at least one of $X^1$, $X^2$, $X^3$ and $X^4$ is nitrogen.

The OLED of the invention includes two electrodes and a light-emitting layer disposed between the two electrodes, wherein the light-emitting layer contains the iridium complex of the invention. The iridium complex may possibly function as a dopant in a host material of the light-emitting layer.

The nitrogen-containing tridentate chelate having a carbene unit of the invention is represented by formula (1), (1)

wherein $R^1$, $R^2$, $R^3$, $R^4$, n, $X^1$, $X^2$, $X^3$ and $X^4$ are defined as above.

As compared to the conventional tris-bidentate iridium complexes, the bis-tridentate iridium complex of the invention has higher rigidity and stability, and therefore improves the luminous efficiency. The iridium complex of the invention also has strong coordination bonding between metal center and ligand so that the transition energy to the metal-centered dd excited states is raised and the non-radiative quenching of phosphorescence is reduced, thus improving the luminous efficiency and the color purity. In addition, the iridium complex of the invention includes carbene as a strong-field ligand, which form stronger bonding with iridium so that the stability of the complex is higher.

In order to make the aforementioned and other objects, features and advantages of the invention comprehensible, a preferred embodiment accompanied with figures is described in detail below.

DESCRIPTION OF EMBODIMENTS

The invention will be further explained with the following embodiments, which are just exemplary and are not intended to limit the scope of the invention.

[Iridium Complex Having a Carbene Fragment]

The iridium complex having a carbene fragment of the invention is represented by formula (I),

(I)

wherein $R^1$ is substituted or unsubstituted $C_{1-12}$ alkyl, or substituted or unsubstituted $C_{6-12}$ aryl; $R^2$ is hydrogen, fluorine or —$C_mF_{2m+1}$ (m=1, 2 or 3), substituted or unsubstituted $C_{1-12}$ alkyl, or substituted or unsubstituted $C_{6-12}$ aryl; $R^3$ is hydrogen, fluorine or —$C_mF_{2m+1}$ (m=1, 2 or 3), substituted or unsubstituted $C_{1-6}$ alkyl, or substituted or unsubstituted $C_{1-6}$ alkoxy, and n is 1, 2, 3 or 4; each of $R^4$ is hydrogen or substituted or unsubstituted $C_{1-12}$ alkyl, or $R^4$'s may join to form a $C_{3-8}$ N-heteroaromatic or aromatic ring, and $R^4$'s may be the same or different; $X^1$, $X^2$, $X^3$ and $X^4$ are each independently CH or nitrogen; $Y^1$, $Y^2$ and $Y^3$ are each independently carbon or nitrogen, with a proviso that at least one of $Y^1$, $Y^2$ and $Y^3$ is nitrogen, and the tridentate chelate $Y^{1\wedge}Y^{2\wedge}Y^3$ is dianionic.

The aromatic ring is an aromatic hydrocarbon ring or an aromatic heterocyclic ring. Specific examples of the aromatic ring include a benzene ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring.

In an embodiment, $R^4$'s may join to form a substituted or unsubstituted benzene ring or a substituted or unsubstituted pyridine ring.

The ligand at the right half of formula (I) is the nitrogen-containing tridentate chelate having a carbene unit of the invention that is represented by formula (1), (1)

wherein $R^1$, $R^2$, $R^3$, $R^4$, n, $X^1$, $X^2$, $X^3$ and $X^4$ are defined as above.

The above tridentate chelate $Y^{1\wedge}Y^{2\wedge}Y^3$ may have at least one electron-withdrawing substituent. The tridentate chelate $Y^{1\wedge}Y^{2\wedge}Y^3$ may be selected from those known in the prior art. The highest occupied molecular orbital (HOMO) of the iridium complex of the invention is adjusted mainly with the tridentate chelate $Y^{1\wedge}Y^{2\wedge}Y^3$. The lowest unoccupied molecular orbital (LUMO) is adjusted mainly with the nitrogen-containing tridentate chelate having a carbene unit of the invention that is represented by the aforementioned formula (1).

When $Y^1$ and $Y^2$ are nitrogen and $Y^3$ is carbon, the iridium complex is represented by formula (I-1),

(I-1)

wherein $R^1$, $R^2$, $R^3$, $R^4$, n, $X^1$, $X^2$, $X^3$ and $X^4$ are defined as in the case of formula (I).

$R^2$ is hydrogen, fluorine or —$C_mF_{2m+1}$ (m=1, 2 or 3), substituted or unsubstituted $C_{1-12}$ alkyl, or substituted or unsubstituted $C_{6-12}$ aryl; $R^3$ may be hydrogen, fluorine or —$C_mF_{2m+1}$ (m=1, 2 or 3), substituted or unsubstituted $C_{1-6}$ alkyl, or substituted or unsubstituted $C_{1-6}$ alkoxy, and n is 1, 2, 3 or 4. When $R^3$ is $C_{1-6}$ alkyl, fluorine or —$C_mF_{2m+1}$ and $X^1$, $X^2$, $X^3$ and $X^4$ are all CH, specific examples of the iridium complexes satisfying formula (I-1) include the following iridium complexes represented by formulas (I-1-1), (I-1-2), (I-1-3), (I-1-4), (I-1-5), (I-1-6) . . . (I-1-24), respectively, abbreviated as compounds (I-1-1), (I-1-2), . . . hereinafter. The abbreviation rule also applies to the later described iridium complexes represented by other chemical structures.

I-1-1

I-1-2

I-1-3

I-1-4

-continued

I-1-5

I-1-6

I-1-7

I-1-8

-continued

I-1-9

I-1-13

I-1-10

I-1-14

I-1-11

I-1-15

I-1-12

I-1-16

I-1-17

I-1-18

I-1-19

I-1-20

I-1-21

I-1-22

I-1-23

I-1-24

When $R^3$ is $C_{1-6}$ alkyl, $C_{1-6}$ alkoxyl, fluorine or $—C_mF_{2m+1}$ and at least one of $X^1$, $X^2$, $X^3$ and $X^4$ is nitrogen, specific examples of the iridium complexes satisfying formula (I-1) included the following iridium complexes represented by formulas (I-1-25), (I-1-26) . . . (I-1-31), respectively. These iridium complexes all have at least one of $X^1$, $X^2$, $X^3$ and $X^4$ being nitrogen, and the design of $X^2$ and/or $X^4$ being nitrogen thereof is capable of increasing the electron-withdrawing effect of the nitrogen-containing tridentate chelate represented by formula (1).

I-1-25

I-1-26

I-1-27

I-1-28

I-1-29

I-1-30

I-1-31

In addition, a case where $Y^1$, $Y^2$ and $Y^3$ in the tridentate chelate $Y^1\char`\^Y^2\char`\^Y^3$ are all nitrogen and a case where $Y^1$ and $Y^3$ are carbon and $Y^2$ is nitrogen are both feasible. Specific examples of the latter case are provided below.

I-a

I-b

I-c

I-d

I-e

I-f

The OLED of the invention includes two electrodes and a light-emitting layer disposed therebetween. The light-emitting layer contains the above iridium complex having a carbene fragment. The material of each of the two electrodes can be selected from commonly used materials in the field, and other functional layers, such as an electron transportation layer and a hole transportation layer, can also be disposed between the electrodes and the light-emitting layer using a known technique in the art. The OLED may be fabricated on a substrate, such as a glass substrate.

[Forming Method of the Iridium Complex Having a Carbene Fragment]

The nitrogen-containing tridentate chelate having a carbene unit of the invention is, for instance, obtained by removing two protons from a precursor thereof. A specific example is shown below, wherein "phimpy" and "phimpy-H$_2$" are symbols used in this specification, "Bu$^t$" represents t-butyl, and "Pr$^i$" represents isopropyl.

$X = I^-, PF_6^-$
(phimpy-H$_2$)X

-continued phimpy

The precursor phimpy-H$_2$ in the above specific example may be prepared with the following method, wherein step (i) uses imidazole, tetrabutylammonium bromide (NBu$_4$Br) and potassium hydroxide as reagents, step (ii) uses 2,4-difluorophenylboronic acid, Pd(dppf)Cl$_2$ and KHCO$_3$ as reagents, step (iii) uses 2-iodopropane as a reagent, and step (iv) uses NH$_4$PF$_6$ as a reagent.

The tridentate chelate Y$^1$^Y$^2$^Y$^3$ in the iridium complex represented by formula (I) may be formed by mixing and reacting a precursor having a corresponding ring structure with a necessary reagent.

The iridium complex having a carbene fragment of the invention can be prepared by adopting suitable reactants and reaction conditions according to the change of each chelate, and the reaction preparation method can be modified based on known techniques in the art. A specific example of the preparation method of the iridium complex contains the following steps. The precursor of the nitrogen-containing tridentate chelate represented by formula (1) of the invention, an iridium source, and other required reagent(s) are mixed, and then the obtained product, a precursor of the tridentate chelate Y$^1$^Y$^2$^Y$^3$, and other required reagent(s) are mixed, and a reaction was caused by heating. The order in which the nitrogen-containing tridentate chelate represented by formula (1) and the tridentate chelate Y$^1$^Y$^2$^Y$^3$ are bonded to the iridium atom can be reversed. That is, the iridium atom and the precursor of the tridentate chelate Y$^1$^Y$^2$^Y$^3$ are reacted first, and then the product and the precursor of the nitrogen-containing tridentate chelate represented by formula (1) are reacted.

EXAMPLE

Certain examples are provided below to further describe the invention, which are merely exemplary and are not intended to limit the scope of the invention.

Synthesis Example 1: Preparation of the Precursor Phimpy-H$_2$ of the Nitrogen-Containing Tridentate Chelate Represented by Formula (1)

X = I$^-$, PF$_6^-$

A mixture of 4-(t-butyl)-2,6-dichloropyridine (1.3 g, 6.37 mmol), imidazole (0.48 g, 7.01 mmol), tetrabutylammonium bromide (1.03 g, 3.18 mmol) and potassium hydroxide (0.43 g, 7.64 mmol) were put in a one-neck flask and then reacted at 80° C. for 12 hours. The obtained imidazolium intermediate was subsequently reacted with 2,4-difluorophenylboronic acid (0.88 g, 5.60 mmol), Pd(dppf)Cl$_2$ (0.11 g, 0.15 mmol), and KHCO$_3$ (2.07 g, 15.00 mmol) in a mixture of toluene (15 mL), ethanol (3 mL), and water (3 mL). The reaction mixture was heated at 110° C. for 12 hours to form 4-(t-butyl)-2-(2,4-difluorophenyl)-6-(1H-imidazol-1-yl)pyridine.

The obtained product (1.15 g, 3.68 mmol) and 2-iodopropane (0.8 mL, 8.07 mmol) were dissolved in toluene (40 mL) and then heated at 110° C. for 12 hours to form an imidazolium iodide pre-ligand. The obtained imidazolium iodide pre-ligand (1.5 g, 3.1 mmol) and NH$_4$PF$_6$ (4.04 g, 25 mmol) were dissolved in ethanol and stirred for 2 hours to perform ion exchange. Addition of water resulted in the precipitation of (phimph-H$_2$)(PF$_6$).

Spectral data of (phimph-H$_2$)(PF$_6$): $^1$H NMR (400 MHz, CDCl$_3$): δ 9.53 (s, 1H), 8.24 (s, 1H), 8.01-7.95 (m, 1H), 7.88 (s, 1H), 7.81 (s, 1H), 7.48 (s, 1H), 7.06-7.02 (m, 1H), 6.97-6.92 (m, 1H), 4.99-4.96 (m, 1H, CH), 1.59 (d, J=6.6 Hz, 3H, Me), 1.58 (d, J=6.6 Hz, 3H, Me), 1.42 (s, 9H, t-Bu). $^{19}$F NMR (376 MHz, CDCl$_3$): δ −70.90 (d, J=712 Hz, PF$_6$), −107.10 (s, 1F), −111.65 (s, 1F).

Example 1: Preparation of Compound (I-1-7)

(I-1-7)

[Ir(COD)(μ-Cl)]$_2$ (300 mg, 0.45 mmol), (phimph-H$_2$) (PF$_6$) (470 mg, 0.94 mmol) and NaOAc (183 mg, 2.23 mmol) were put in a two-neck flask and reacted at 80° C. for 12 hours, using anhydrous acetonitrile (20 mL) as a solvent. After the temperature was lowered to room temperature and the solvent was evaporated, 2-(5-trifluoromethyl-1H-pyrazol-3-yl)-6-(4-fluorophenyl)pyridine (316 mg, 1.03 mmol) and sodium acetate (366 mg, 4.47 mmol) were added, and the mixture was dissolved in decahydronaphthalene (20 mL) and reacted at 200° C. for 24 hours. After the reaction was finished, purification was done by column chromatography to obtain a product (yield: 23%).

Spectral data of compound (I-1-7): $^1$H NMR (400 MHz, CDCl$_3$): δ 8.14 (s, 1H), 7.76 (t, J=8.0 Hz, 1H), 7.60-7.55 (m, 4H), 7.37 (s, 1H), 6.91 (s, 1H), 6.79 (d, J=2.4 Hz, 1H), 6.56-6.51 (m, 1H), 6.32-6.26 (m, 1H), 5.53 (d, J=8.0 Hz, 2H), 3.53-3.29 (m, 1H, CH), 1.54 (s, 9H, t-Bu), 0.80 (d, J=6.8 Hz, 3H, Me), 0.74 (d, J=6.8 Hz, 3H, Me). $^{19}$F NMR (376 MHz, CDCl$_3$): δ −59.81 (s, 3F), −107.49 (d, J=9.8 Hz, 1F), −110.48 (d, J=9.8 Hz, 1F), 110.52 (s, 1F). MS [FAB]: m/z 852.6, M$^+$. Anal. Calcd. for C$_{36}$H$_{29}$F$_6$IrN$_6$: C, 50.76; H, 3.43; N, 9.87. Found: C, 50.64; H, 3.77; N, 9.48.

Example 2: Preparation of Compound (I-1-8)

(I-1-8)

The synthesis steps of compound (I-1-8) was similar to those of compound (I-1-7), except that 2-(5-trifluoromethyl-1H-pyrazol-3-yl)-6-(4-fluorophenyl)pyridine was replaced by 2-(5-trifluoromethyl-1H-pyrazol-3-yl)-6-(4-trifluoromethylphenyl)pyridine. The yield of compound (I-1-8) was 26%.

Spectral data of compound (I-1-8): $^1$HNMR (400 MHz, CDCl$_3$): δ 8.15 (s, 1H), 7.81 (t, J=8.0 Hz, 1H), 7.72 (d, J=8.0 Hz, 1H), 7.67 (d, J=8.0 Hz, 1H), 7.64 (d, J=8.0 Hz, 1H), 7.58 (s, 1H), 7.39 (s, 1H), 7.05 (d, J=8.0 Hz, 1H), 6.93 (s, 1H), 6.81 (s, 1H), 6.33-6.27 (m, 1H), 6.05 (s, 1H), 5.49 (s, 1H), 3.33-3.27 (m, 1H, CH), 1.53 (s, 9H, t-Bu), 0.80 (d, J=6.8 Hz, 3H, Me), 0.74 (d, J=6.8 Hz, 3H, Me). $^{19}$F NMR (376 MHz, CDCl$_3$): δ −59.89 (s, 3F), −62.81 (s, 3F), −107.42 (d, J=9.8 Hz, 1F), −110.35 (d, J=9.8 Hz, 1F). MS [FAB]: m/z 902.7, M. Anal. Calcd. for C$_{37}$H$_{29}$F$_8$IrN$_6$: C, 49.28; H, 3.24; N, 9.32. Found: C, 49.29; H, 3.33; N, 8.91.

Example 3: Preparation of Compound (I-1-9)

(I-1-9)

IrCl$_3$.3H$_2$O (200 mg, 0.57 mmol) and (phimph-H$_2$)(PF$_6$) (313 mg, 0.62 mmol) were put in a one-neck flask and reacted at 120° C. for 12 hour, using 2-methoxyethanol (15 mL) as a solvent, and then the temperature was lowered to room temperature. After the solvent was evaporated, 2-(5-trifluoromethyl-1H-pyrazol-3-yl)-6-(4-t-butylphenyl)pyridine (215 mg, 0.62 mmol) and NaOAc (209 mg, 2.55 mmol) were added, and the mixture was dissolved in decahydronaphthalene (20 mL) and reacted at 200° C. for 24 hours. After the reaction was finished, purification was done by column chromatography to obtain a product (yield: 23%).

Spectral data of compound (I-1-9): $^1$H NMR (400 MHz, CDCl$_3$): δ 8.13 (s, 1H), 7.72 (t, J=8.0 Hz, 1H), 7.59-7.56 (m, 3H), 7.46-7.44 (m, 2H), 6.92 (s, 1H), 6.82 (dd, J=8.0 Hz, 2.0 Hz, 1H), 6.73 (d, J=2.0 Hz, 1H), 6.30-6.24 (m, 1H), 5.64 (d, J=2.0 Hz, 1H), 5.60 (dd, J=8.0 Hz, 2.0 Hz, 1H), 3.39-3.32 (m, 1H), 1.50 (s, 9H, t-Bu), 0.92 (s, 9H, t-Bu), 0.81 (d, J=6.8 Hz, 3H, Me), 0.69 (d, J=6.8 Hz, 3H, Me). $^{19}$F NMR (376 MHz, CDCl$_3$): δ −59.77 (s, 3F), 107.80 (d, J=9.8 Hz, 1F), −111.36 (d, J=9.8 Hz, 1F). MS [FAB]: m/z, 890.7 M$^+$.

Example 4: Preparation of Compound (I-1-10)

(I-1-10)

The synthesis steps of compound (I-1-10) was similar to those of compound (I-1-7), except that 2-(5-trifluoromethyl-1H-pyrazol-3-yl)-6-(4-fluorophenyl)pyridine was replaced by 2-(5-trifluoromethyl-1H-pyrazol-3-yl)-6-(1-naphthyl)pyridine. The yield of compound (I-1-10) was 35%.

Spectral data of compound (I-1-10): $^1$HNMR (400 MHz, CDCl$_3$): δ 8.61 (d, J=8.0 Hz, 1H), 8.38 (d, J=8.0 Hz, 1H), 8.17 (s, 1H), 7.82 (t, J=8.0 Hz, 1H), 7.65-7.60 (m, 2H), 7.56 (d, J=2.0 Hz, 1H), 7.48 (t, J=8 Hz, 1H), 7.41 (s, 1H), 7.28 (t, J=8.0 Hz, 1H), 7.10 (d, J=8.0 Hz, 1H), 6.94 (s, 1H), 6.73 (d, J=2.0 Hz, 1H), 6.28-6.22 (m, 1H), 6.11 (d, J=8.0 Hz, 1H) 5.45 (d, J=8.0 Hz, 1H), 3.45-3.39 (m, 1H, CH), 1.55 (s, 1H, t-Bu), 0.76 (d, J=6.8 Hz, 3H, Me), 0.73 (d, J=6.8 Hz, 3H, Me). $^{19}$F NMR (376 MHz, CDCl$_3$): δ −59.75 (s, 3F), −107.24 (d, J=9.8 Hz, 1F), −110.65 (d, J=9.8 Hz, 1F). MS [FAB]: m/z, 884.5 M. Anal. Calcd. for C$_{40}$H$_{32}$F$_5$IrN$_6$: C, 54.35; H, 3.65; N, 9.51. Found: C, 54.26; H, 4.06; N, 8.90.

Example 5: Preparation of Compound (I-1-11)

(I-1-11)

[Ir(COD)(μ-Cl)]$_2$ (118 mg, 0.18 mmol), (phimph-H$_2$)(PF$_6$) (186 mg, 0.37 mmol) and NaOAc (72 mg, 0.88 mmol) were put in a two-neck flask and reacted at 80° C. for 12 hours, using anhydrous acetonitrile (10 mL) as a solvent. After the temperature was lowered to room temperature and the solvent was evaporated, 2-(5-trifluoromethyl-1H-pyrazol-3-yl)-6-phenylisoquinoline (120 mg, 0.36 mmol) and NaOAc (144 mg, 1.76 mmol) were added, and the mixture dissolved in xylene (25 mL) and reacted at 160° C. for 24 hours. After the reaction was finished, purification was done by column chromatography to obtain a product (yield: 27%).

Spectral data of compound (I-1-11): $^1$HNMR (400 MHz, CDCl$_3$): δ 8.95 (d, J=8.0 Hz, 1H), 8.32 (d, J=8.0 Hz, 1H), 8.14 (s, 1H), 8.05 (d, J=7.6 Hz, 1H), 7.98 (s, 1H), 7.73-7.67 (m, 2H), 7.56 (d, J=2.0 Hz, 1H), 7.39 (s, 1H), 6.94 (s, 1H), 6.93 (t, J=6.8 Hz, 1H), 6.75 (d, J=2.0 Hz, 1H), 6.71 (t, J=7.6 Hz, 1H), 6.28-6.22 (m, 1H), 6.06 (d, J=6.8 Hz, 1H), 5.45 (m, 1H), 3.34-3.27 (m, 1H, CH), 1.54 (s, 9H, t-Bu), 0.72 (d, J=6.8 Hz, 3H, Me), 0.66 (d, J=6.8 Hz, 3H, Me). $^{19}$F NMR (376 MHz, CDCl$_3$): δ −59.65 (s, 3F), −107.69 (d, J=9.8 Hz, 1F), −110.85 (d, J=9.8 Hz, 1F). MS [FAB]: m/z, 884.3 M$^+$.

Example 6: Preparation of Compound (I-1-13)

(I-1-13)

[Ir(COD)(μ-Cl)]$_2$ (50 mg, 0.07 mmol), (phimph-H$_2$)(PF$_6$) (75 mg, 0.15 mmol) and NaOAc (62 mg, 0.76 mmol) were put in a two-neck flask and reacted at 80° C. for 12 hours, using anhydrous acetonitrile (10 mL) as a solvent. After the temperature was lowered to room temperature and the solvent was evaporated, 4-tert-butyl-2-phenyl-6-(3-(trifluoromethyl)-1H-5-pyrazolyl) pyrimidine (52 mg, 0.15 mmol) and NaOAc (144 mg, 1.76 mmol) were added, and the mixture dissolved in xylene (25 mL) and reacted at 160° C. for 24 hours. After the reaction was finished, purification was done by column chromatography to obtain a product (yield: 31%).

Spectral data of compound (I-1-13): $^1$HNMR (400 MHz, CDCl$_3$): δ 8.14 (s, 1H), 8.04 (d, J=7.4 Hz, 1H), 7.54 (s, 1H), 7.51 (s, 1H), 7.36 (s, 1H), 7.07 (s, 1H), 6.87 (t, J=7.4 Hz, 1H), 6.77-6.72 (m, 2H), 6.28 (t, J=9.6 Hz, 1H), 5.86 (d, J=7.4 Hz, 1H), 5.54 (dd, J=3.8, 2.2 Hz, 1H), 3.29-3.22 (m, 1H, CH), 1.53 (s, 9H, t-Bu), 0.72 (d, J=6.8 Hz, 3H, Me), 0.66 (d, J=6.8 Hz, 3H, Me); $^{19}$F NMR (376 MHz, CDCl$_3$): δ −59.92 (s, 3F), −107.51 (d, J=9.8 Hz, 1F), −110.57 (d, J=9.8 Hz, 1F); MS [FAB]: m/z, 891.3 M.

Figure 1:
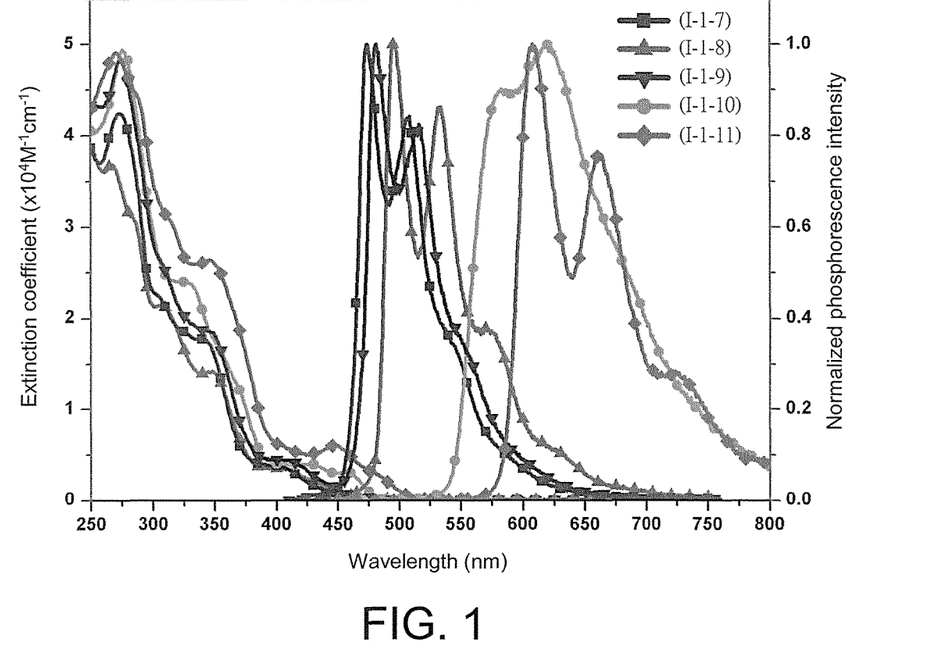
FIG. 1 shows the absorption spectra and the phosphorescence spectra of the carbene-containing iridium complexes synthesized in Examples 1 to 5 of the invention.

The absorption spectra and the phosphorescence spectra of the iridium complexes (I-1-7) to (I-1-11) that were synthesized in Examples 1 to 5 are shown in FIG. 1, and the absorption peak location (abs $λ_{abs}$), the emission peak location ($λ_{em}$), the quantum yield (φ), and the phosphorescence lifetime (τ) thereof are listed in Table 1 below.

| Compound | $λ_{abs}$/nm (ε × 10$^4$ M$^{-1}$cm$^{-1}$)$^a$ | $λ_{em}$/nm$^b$ | φ (%)$^{b,\,c}$ | $τ_{obs}$/μs$^b$ |
|---|---|---|---|---|
| (I-1-7) | 304 (2.25), 340 (1.77), 398 (0.38) | 473, 508 | 99 | 3.10 |
| (I-1-8) | 311 (2.1), 350 (1.40), 410 (0.34) | 495, 534, 574 (sh) | 91 | 3.91 |
| (I-1-9) | 310 (2.53), 343 (1.81), 408 (0.44) | 481, 515 | ~100 | 3.01 |
| (I-1-10) | 330 (2.38), 430 (0.4), 458 (0.31) | 583, 618 | 25 | 9.23 |
| (I-1-11) | 345 (2.64), 448 (0.60), 481 (0.29) | 608, 663, 725 (sh) | 57 | 5.40 |

$^a$Measured in CH$_2$Cl$_2$ in a concentration of 10$^{-5}$ M.
$^b$Measured in degassed CH$_2$Cl$_2$ solution.
$^c$ Coumarin (C153) in EtOH (Φ = 58% and $λ_{max}$ = 530 nm) and 4-(dicyanomethylene)-2-methyl-6-(4-dimethylaminostyryl)-4H-pyran in DMSO (Φ = 80% and $λ_{max}$ = 637 nm) were employed as standard.

It is clear from FIG. 1 and Table 1 that compounds (I-1-7), (I-1-8) and (I-1-9) have high quantum yields, and compounds (I-1-10) and (I-1-11) in which the tridentate chelate C^N^N' further include a benzo-ring can enhance conjugation of the chromophore to reduce the energy gap and make a red shift of the emitted light.

Other effects of the above compounds are described below. As compared to the N—Ir bonding formed by coordination of a pyridine ligand to iridium, the C—Ir bonding formed by coordination of carbene as a strong-field ligand to iridium is stronger, so that the stability of the complex is higher. Regarding the luminous performance, the strong coordination bonding can raise the transition energy to the metal-centered dd excited states and to reduce the non-radiative quenching of phosphorescence, thus improving the luminous efficiency and the color purity. In addition, as compared to the conventional tris-bidentate iridium complexes, the bis-tridentate iridium complex of the invention has higher rigidity, and therefore improves the luminous efficiency and the device stability.

Example 7

Figure 2:
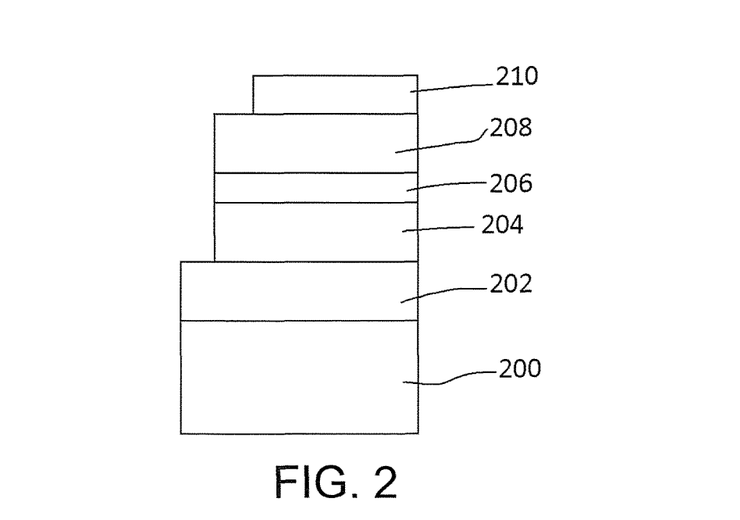
FIG. 2 illustrates the OLED structure for measuring the luminescence characteristics of the iridium complexes in Example 7 of the invention.

An OLED was fabricated using one of the iridium complexes of the invention. The structure thereof was schematically illustrated in FIG. 2, including a glass substrate 200, an anode 202, a hole transportation layer 204, a light-emitting layer 206, an electron transportation layer 208 and a cathode 210. The material of the anode 202 is ITO. The material of the hole transportation layer 204 is TAPC. The material of the light-emitting layer 206 is mCP doped with the iridium complex of the invention. The material of the electron transportation layer 208 is TmPyPB. The material of the cathode 210 is LiF/Al.

As mentioned above, the iridium complex of the invention has strong coordination bonding so that the transition energy to the metal-centered dd excited states is raised and the non-radiative of phosphorescence is reduced, thus improving the luminous efficiency and the color purity. In addition, the iridium complex of the invention includes carbene as a strong-field ligand, which form stronger bonding with iridium so that the stability of the complex is higher.

The invention has been disclosed above in the preferred embodiments, but is not limited to those. It is known to persons skilled in the art that some modifications and innovations may be made without departing from the spirit and scope of the invention. Hence, the scope of the invention should be defined by the following claims.

What is claimed is:

1. An iridium complex, being represented by formula (I):

(I)

wherein $R^1$ is substituted or unsubstituted $C_{1-12}$ alkyl, or substituted or unsubstituted $C_{6-12}$ aryl; $R^2$ is hydrogen, fluorine or —$C_mF_{2m+1}$ (m=1, 2 or 3), substituted or unsubstituted $C_{1-12}$ alkyl, or substituted or unsubstituted $C_{6-12}$ aryl; $R^3$ is hydrogen, fluorine or —$C_mF_{2m+1}$ (m=1, 2 or 3), substituted or unsubstituted $C_{1-6}$ alkyl, or substituted or unsubstituted $C_{1-6}$ alkoxy, and n is 1, 2, 3 or 4; each of $R^4$ is hydrogen or substituted or unsubstituted $C_{1-12}$ alkyl, or $R^4$'s may join to form a $C_{3-8}$ N-heteroaromatic or aromatic ring, and $R^4$'s may be the same or different; $X^1$, $X^2$, $X^3$ and $X^4$ are each independently CH or nitrogen; $Y^1$ is nitrogen in a pyrazole ring as a part of the tridentate chelate $Y^1{\char'136}Y^2{\char'136}Y^3$, $Y^2$ and $Y^3$ are each independently carbon or nitrogen, and the tridentate chelate $Y^1{\char'136}Y^2{\char'136}Y^3$ is dianionic.

2. The iridium complex of claim 1, wherein the tridentate chelate $Y^1{\char'136}Y^2{\char'136}Y^3$ has at least one electron-withdrawing substituent.

3. The iridium complex of claim 1, wherein is nitrogen and $Y^3$ is carbon, the iridium complex being represented by formula (I-1):

(I-1)

wherein $R^1$, $R^2$, $R^3$, $R^4$, n, $X^1$, $X^2$, $X^3$ and $X^4$ are defined as in claim 1.

4. The iridium complex of claim 1, wherein $X^1$, $X^2$, $X^3$ and $X^4$ are all CH.

5. The iridium complex of claim 4, being represented by any one of formulae (I-1-1) to (I-1-24):

I-1-1

-continued

I-1-2

I-1-3

I-1-4

I-1-5

-continued

I-1-6

I-1-7

I-1-8

I-1-9

-continued

I-1-10

I-1-11

I-1-12

I-1-13

-continued

I-1-14

I-1-15

I-1-16

I-1-17

I-1-18

I-1-19

I-1-20

I-1-21

I-1-22

I-1-23

I-1-24

6. The iridium complex of claim 1, wherein at least one of $X^1$, $X^2$, $X^3$ and $X^4$ is nitrogen.

7. The iridium complex of claim 6, being represented by any one of formulae (I-1-25) to (I-1-31):

I-1-25

I-1-26

I-1-27

I-1-28

-continued

I-1-29

I-1-30

I-1-31

8. The iridium complex of claim 1, having a structure represented by one of formulae (I-a) and (I-b):

I-a

-continued

I-b

9. An organic light-emitting diode, comprising two electrodes and a light-emitting layer disposed between the two electrodes, wherein the light-emitting layer contains the iridium complex of claim 1.

10. The organic light-emitting diode of claim 9, wherein the iridium complex functions as a dopant in a host material of the light-emitting layer.

11. An N-containing tridentate chelate having a carbene unit, represented by formula (1):

(1)

wherein $R^1$ is substituted or unsubstituted $C_{1-12}$ alkyl, or substituted or unsubstituted $C_{6-12}$ aryl; $R^2$ is hydrogen, fluorine or —$C_mF_{2m+1}$ (m is 1, 2 or 3), substituted or unsubstituted $C_{1-12}$ alkyl, or substituted or unsubstituted $C_{6-12}$ aryl; $R^3$ is hydrogen, fluorine or —$C_mF_{2m+1}$ (m=1, 2 or 3), substituted or unsubstituted $C_{1-6}$ alkyl, or substituted or unsubstituted $C_{1-6}$ alkoxy, and n is 1, 2, 3 or 4; each of $R^4$ is hydrogen or substituted or unsubstituted $C_{1-12}$ alkyl, or $R^4$'s may join to form a $C_{3-8}$ N-heteroaromatic or aromatic ring, and $R^4$'s may be the same or different; $X^1$, $X^2$, $X^3$ and $X^4$ are each independently CH or nitrogen, wherein at least one of $X^1$, $X^2$, $X^3$ and $X^4$ is nitrogen.

* * * * *